United States Patent [19]
Larkin et al.

[11] Patent Number: 5,437,650
[45] Date of Patent: Aug. 1, 1995

[54] SECURING COLLAR FOR CANNULA CONNECTOR

[75] Inventors: Mark E. Larkin, Lindenhurst; Dvid E. Kramer, Northbrook; Warren P. Frederick, Wonder Lake, all of Ill.

[73] Assignee: Abbott Laboratories, Abbott Park, Ill.

[21] Appl. No.: 371,317

[22] Filed: Jan. 11, 1995

Related U.S. Application Data

[63] Continuation of Ser. No. 129,233, Sep. 29, 1993, abandoned, which is a continuation-in-part of Ser. No. 36,005, Mar. 23, 1993, abandoned.

[51] Int. Cl.⁶ .................... A61M 25/00; F16L 21/06
[52] U.S. Cl. .................... 604/283; 285/322; 604/905
[58] Field of Search .......... 604/83, 86, 88, 167, 604/256, 283, 284, 905; 285/24, 315, 27, 322

[56] References Cited

U.S. PATENT DOCUMENTS

| | | | |
|---|---|---|---|
| 2,784,987 | 3/1957 | Corcoran | 285/315 X |
| 3,394,950 | 7/1968 | Jenson | 285/322 X |
| 3,413,021 | 11/1968 | Potts | 285/322 X |
| 3,565,078 | 2/1971 | Vaillancourt | 604/256 |
| 4,103,941 | 8/1978 | Stoll | 285/238 |
| 4,323,065 | 4/1982 | Kling | 285/322 X |
| 4,329,987 | 5/1982 | Rogers et al. | 604/283 |
| 4,405,163 | 9/1983 | Voges et al. | 285/305 |
| 4,723,948 | 2/1988 | Clark et al. | 604/283 |
| 4,895,570 | 1/1990 | Larkin | 64/411 |
| 4,950,254 | 8/1990 | Andersen et al. | |
| 5,052,386 | 10/1991 | Fischer, Jr. | 128/207.15 |
| 5,120,324 | 6/1992 | Sancoff | 604/283 |
| 5,137,524 | 8/1992 | Lynn et al. | 604/283 |
| 5,197,895 | 3/1993 | Stupecky | 439/194 |
| 5,242,431 | 9/1993 | Kristiansen | 604/283 |
| 5,248,306 | 9/1993 | Clark et al. | 604/283 |
| 5,273,533 | 12/1993 | Bonaldo | |
| 5,281,206 | 1/1994 | Lopez | |
| 5,312,377 | 5/1994 | Dalton | |

OTHER PUBLICATIONS

*The Random House College Dictionary: Revised Edition,* (Random House, Inc., 1980), pp. 55, 1137–1138.

*Primary Examiner*—John D. Yasko
*Assistant Examiner*—Adam J. Cemak
*Attorney, Agent, or Firm*—A. Nicholas Trausch, III

[57] ABSTRACT

A securing collar is used in combination with two tubular flow connectors to prevent the inadvertent disconnection of I.V. tubing sets. The securing collar includes a housing supported by one of the connectors, a radial flange extending from the housing, a tubular collar having a outwardly splayed end, at least two notches that separates the splayed collar into at least two elongated segments, a transition portion on the exterior of the collar, and a sliding annular locking ring. The locking ring slides on the collar from the proximal end over the transition portion to the distal segments so that the annular locking ring forces the splayed and segmented distal portions radially inward to grip the second connector.

15 Claims, 7 Drawing Sheets

SECURING COLLAR FOR CANNULA CONNECTOR

This application is a continuation of application Ser. No. 08/129,233, filed Sep. 29, 1993, now abandoned, which is a continuation in part of application Ser. No. 08/036,005, filed on Mar. 23, 1993 and assigned to the same assignee (now abandoned).

BACKGROUND OF THE INVENTION

The present invention relates to a securing apparatus which can be used to prevent the unintentional disengagement of two medical tubing connectors in fluid flow. More particularly, the invention relates to a securing collar having a splayed collar and a sliding locking ring used to secure a cannula connector to a reseal connector for fluid flow communication with IV tubing.

In general, intravenous fluid flow involves the gravity or pump-assisted flow of a medical solution from a sterile source container through a sterile tubing set to a patient's vein. Usually at least one sterile connection must be made and maintained to effectively and safely transfer the medical solution from the container to the patient. A sterile connection with an intravenous tubing set can be made in a variety of ways. The traditional and most commonly used fluid flow connection is made using a sharp needle associated with the first connector to pierce a resealable elastomeric septum of a second connector. Recently, due to the concerns about accidental needle sticks, a blunt cannula connector such as the LifeShield ® Blunt Cannula sold by Abbott Laboratories, rather than the traditional sharp needle connector is being used. The blunt cannula connector is used with a prepierced or partially pierced elastomeric septum connector, such as the LifeShield ® Prepierced Reseal, also sold by Abbott Laboratories.

A primary concern with any medical tubing connector is the accidental or unintentional disengagement of the connector. A sharp or blunt cannula can accidentally be pulled out of a reseal. An accidental disconnection can contaminate the cannula of the connector and/or allow the medical solution to spill or drain. In addition to the interruption in the intravenous therapy, accidental disconnection may compromise the sterility and integrity of the IV flow system. Contaminants may be introduced into the IV flow system if the connectors are reconnected without effective disinfecting.

The above concerns have led to medical guidelines and procedures that suggest and sometimes require that I.V. tubing connections be secured together. A variety of known devices are currently used for securing I.V. tubing connections. However, many of the known securing apparatus are undesirable, for example, because of their bulk, complexity and/or expense. Furthermore, there are other concerns such as patient discomfort, the amount of time and manipulation required from the health care provider to attach and release the securing apparatus, or the lack of effectiveness in preventing disconnections.

Tape is often used in addition to or when no suitable securing apparatus is available. However, tape has an inherent drawback when the connectors need to be quickly disconnected. Also, tape is awkward to use when one of the connectors is in close proximity to the patient's body such as the connector at the vein access site. Excessive movement of the connector at the vein access site, for example, can cause patient discomfort or damage to the vein wall.

Thus, there is a need for a simple, inexpensive, yet reliable securing apparatus that can reduce accidental disengagement of I.V. tubing connectors. It is desirable that the securing apparatus be readily engageable and disengageable. Further, it is desirable that the securing apparatus be easy to manipulate and compatible with different fluid flow connectors. Finally, it is desirable that the securing apparatus be usable with blunt cannula or sharp needle connectors.

SUMMARY OF THE INVENTION

Therefore it is a primary object of this invention to provide a simple and reliable construction for a securing apparatus used in combination with intravenous fluid flow connectors.

It is another object of this invention to provide a securing apparatus for use with intravenous tubing connectors such as either a sharp needle or a blunt cannula and their respective resealable and prepierced septums.

It is a further object of this invention to provide a securing apparatus that is easy to manipulate by the health care provider, yet reliable in securing the connectors of the intravenous tubing set.

The present invention relates to a securing apparatus for a tubing connector which secures the cannula of one connector to the reseal septum of a second connector. The first tubing connector is of the type having an axially extending hub and a cannula coaxially extending from the hub. The securing apparatus includes a radial flange generally radially extending from the connector hub. A frustoconical splayed tubular collar includes a first tubular portion longitudinally extending from the radial flange and a second tubular portion further extending from the first tubular portion. The splayed collar has preferably two longitudinal notches in the splayed collar for dividing the collar into longitudinal segments. An annular locking ring is slidable on the collar from the first tubular portion to the second tubular portion. The second tubular portion of the splayed collar is constructed and arranged such that the annular locking ring forces at least the second tubular portion of the splayed collar radially inward as the locking ring moves from the first tubular portion to the second tubular portion.

In a preferred embodiment, the outside diameter of the second tubular portion is larger than the outside diameter of the first tubular portion which forces at least the second tubular portion radially inward as the annular locking ring is slid to the second tubular portion. A transition portion of the collar is constructed between the first and second tubular portions to retain the annular locking ring on the second tubular portion. The transition portion includes a retaining portion that has a larger outer dimension than the outer diameter of the second tubular portion. The restraining portion preferably is a set of discrete bumps circumferentially positioned adjacent the longitudinal notches.

The securing collar also includes structure for limiting rotation of the annular locking ring relative to the tubing connector when the annular locking ring is positioned on the first tubular portion, as for example, when the connector is initially attached to the IV tubing set. Preferably this rotation limiting structure is a raised longitudinal tab on an outer surface of the first tubular portion and a mating slot on an inner surface of the annular locking ring.

The second tubular portion of the tubular collar also has an undercut flange on a distal end of the inner surface of the collar for engaging a second connector when the second tubular portion is forced radially inward by the annular locking ring.

In a preferred embodiment, the securing apparatus of the present invention is integrally manufactured as a splayed collar supported by the hub of the cannula connector.

In another embodiment, the securing apparatus is manufactured separately and can be added later to an individual cannula connector, either in the assembly plant or in the hospital, for example.

Generally, either of the above construction allows the securing apparatus to secure the first flow connector to the second flow connector and restrain the cannula of the first connector from being inadvertently pulled from the reseal septum of the second connector.

Other features and advantages of the present invention will become readily apparent from the following detailed description, the accompanying drawings, and the appended claims.

DESCRIPTION OF A PREFERRED EMBODIMENT

Figure 1:
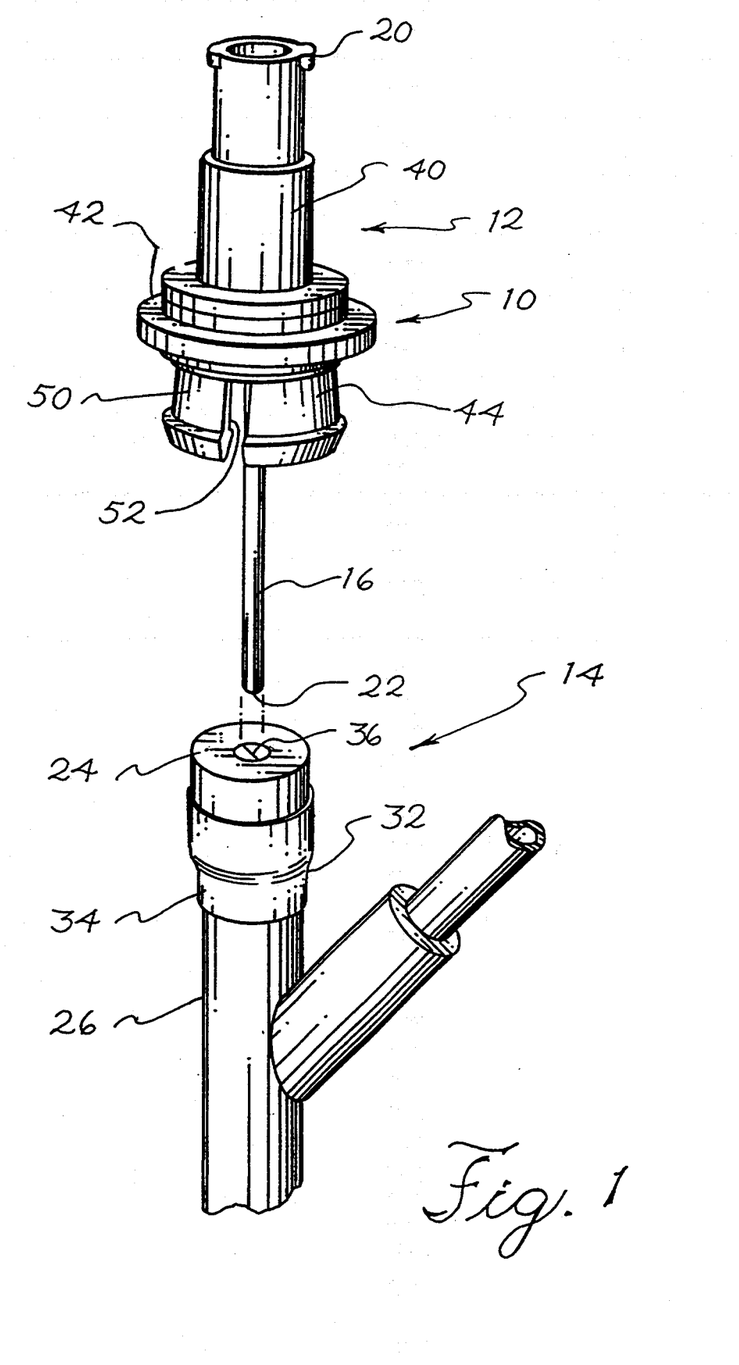
FIG. 1 is a perspective view of two unengaged fluid flow connectors including a blunt cannula connector with a securing collar according to one embodiment of the present invention and a connectable prepierced reseal septum connector.

Referring now to FIG. 1, a first fluid flow connector 12 for connection of intravenous tubing is shown with a second fluid flow connector 14. The first connector 12 is a male connector such as a LifeShield ® Blunt Cannula and the second connector 14 is a female connector such as a LifeShield Prepierced Reseal Y-Site, both of which are sold by Abbott Laboratories. A securing apparatus 10 according to the present invention is associated with the first connector 12.

Figure 2:
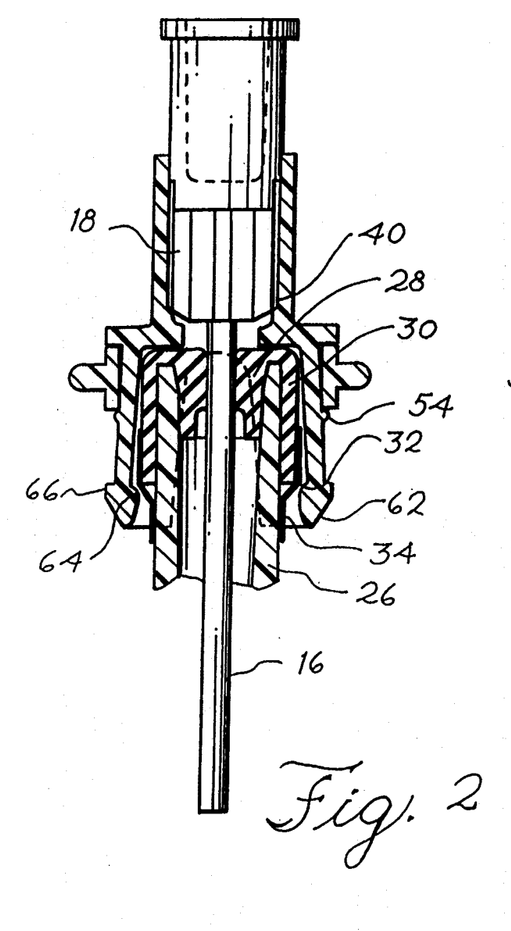
FIG. 2 is a cross-section of the connectors of FIG. 1 with the connectors now engaged in fluid flow communication and with the securing collar according to the present invention in the unsecured position.
Figure 3:
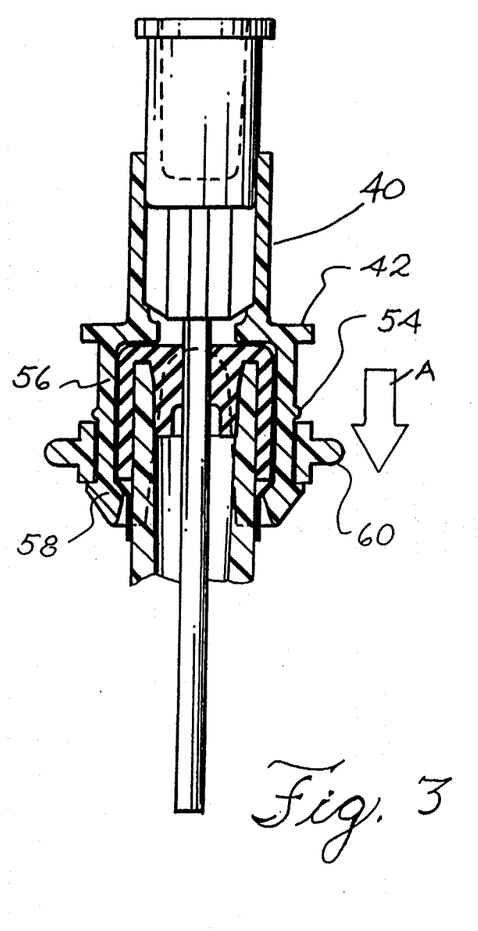
FIG. 3 is a cross-section of the engaged connectors similar to FIG. 2 with the securing collar of the present invention in the secured position.
Figure 6:
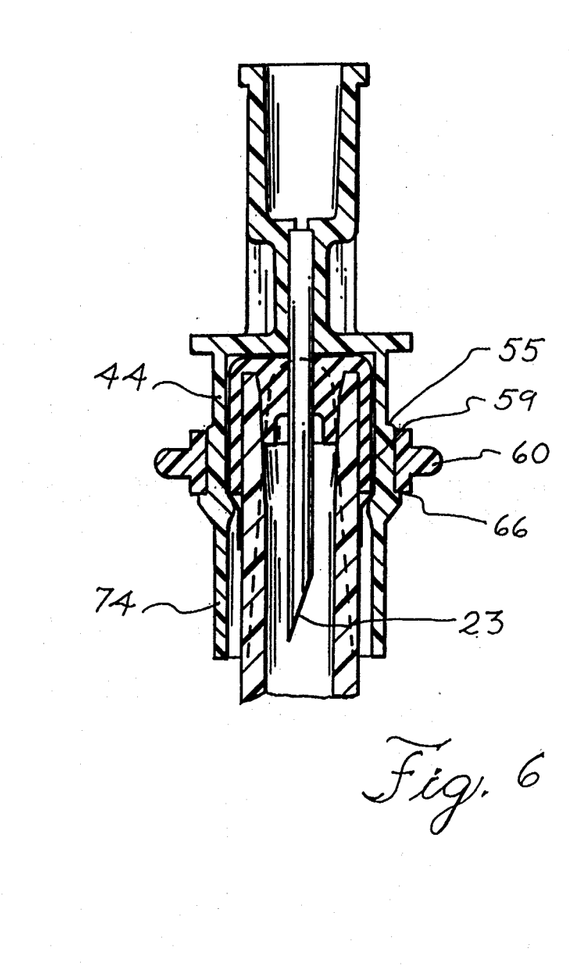
FIG. 6 is a cross-section similar to FIG. 4 showing other alternate embodiments of the present invention including a shroud portion extending concurrently with a sharp cannula.

Referring now to FIGS. 1-3, the first connector 12 includes a cannula 16 which is preferably made of stainless steel. The cannula is coaxially secured in a molded plastic cannula hub 18 by adhesive or other known securing techniques. A luer fitment 20 at the upstream end of the cannula connector 12 permits the connector to be connected to a standard I.V. tubing set. The delivery end of the cannula 16 can be blunt 22, as shown in FIG. 1, or alternatively can be sharp 23, as shown in FIG. 6.

The second connector 14 includes a reseal septum 24 connectable in fluid flow communication with the cannula 16 of the first connector 12. The reseal connector includes a rigid plastic tubular housing 26 for holding the elastomeric reseal 24. As shown in FIGS. 2 and 3, the reseal 24 includes a plug portion 28 that is inserted into the interior of the rigid tubular housing 26 and an exterior rolled-over portion 30 which is folded down on the outside of the rigid tubular housing 26. The rolled-over portion of the reseal forms a radially raised annular shoulder 32 on the outer surface of the tubular housing 26. Typically a shrink band 34 is provided over the juncture of the rolled-over portion 30 of the reseal and the tubular housing 26. Alternatively, the second connector 14 may have a radial shoulder integrally formed on the exterior surface of the tubular housing 26.

The reseal 24 is preferably made of an elastomeric material such as a medical grade latex rubber that can be sterilized. The reseal septum may include an unpierced diaphragm portion (not shown) that is first pierced by a sharp cannula or may include a prepierced diaphragm portion 36, such as the previously mentioned LifeShield Prepierced Reseal sold by Abbott Laboratories for use with a blunt cannula.

The securing apparatus 10 includes a tubular housing portion 40 for axially supporting or engaging the hub 18 of the first connector 12. A generally radially extending deflectably flange 42 extends radially from the housing 40. A tubular collar 44 extends longitudinally forward from the radial flange 42. The tubular collar is coaxial with the cannula 16. The collar is also coaxial and oppositely extending from the tubular housing 40.

The collar 44 is frustoconical or splayed or normally outwardly spreading in the axially forward direction. The splayed collar includes at least two longitudinally extending recesses or notches 52 which divide the splayed collar into at least two longitudinal collar segments 50. As shown in FIG. 1, for example, two diametrically opposite recesses or notches 52 divide the splayed tubular collar 44 into two splayed collar segments 50. For manufacturing purposes, fewer than two recesses and segments may be desirable. For functional securing purposes, more than two recesses and segments may be preferred.

The tubular collar 44 includes a transition portion 54 (as seen in FIGS. 2 and 3) that longitudinally divides the splayed tubular collar 44 into a first (or proximal) splayed tubular portion 56 and a second (or distal) splayed tubular portion 58. The first splayed tubular portion 56 circumferentially extends from the radial flange 42. The second splayed tubular portion 58 further extends from the first splayed tubular portion 56. The transition portion 54 may be a small annular protrusion located approximately midway on the outer surface of the tubular collar 44, as shown in FIGS. 2 and 3 for example. Alternatively, as shown in FIG. 6, the transition portion may be an integral shoulder 55 of a larger diameter outer surface of a modified second tubular portion 59 of the splayed collar 44.

Referring again to FIGS. 1-3, an annular locking ring 60 is slidable along the outer surface of the splayed collar 44 from the first tubular portion 56 to the second tubular portion 58. When the first connector 12 is engaged with the second connector 14 and the annular locking ring 60 is positioned on the first tubular portion 56 as shown in FIG. 2, the splayed segments 50 of the second tubular portion 58 of the collar are angled outwardly and can not reliably grip the annular shoulder 32 on the second connector 14. However, when the annular locking ring 60 is advanced past the transition portion 54 to a position over the second portion 58 of the splayed collar, as shown by arrow A in FIG. 3, the change in position forces at least the second tubular portion 58 of the splayed segments 50 radially inward to retain or grip the second connector 14, preferably at the shoulder 32.

The manual manipulation required by the healthcare worker to slide the annular locking ring 60 to the forward secured position is simply a continuation of the motion required to engage the connectors 12 and 14 together. Thus, the securing collar 10 of the present invention is easily and readily connected while providing enough axial resistance for the cannula connector 12 such that the cannula is not unintentionally withdrawn from the septum connector 14.

The splayed tubular collar 44 preferably has an undercut or inward lip 64 on the distal inner surface, so that the undercut can engage the raised shoulder 32 on the mating connector. The collar also preferably includes an external lip 66 on the second portion 58 to prevent the annular locking ring 60 from sliding completely off the splayed segments 50 when the annular locking ring 60 is being advanced toward the secured (or locked) position. A radially outwardly orientated flange, such as flange 42 at the other end of the collar prevents annular locking ring 60 from being pulled completely off the collar when the annular locking ring 60 is retracted to the unsecured (or unlocked) position.

The transition portion 54 on the tubular collar 44 retains the annular locking ring 60 in the unsecured position until sufficient force is applied to the annular locking ring 60 to cause the ring to move over the transition portion 54. The tapered lead-in 62 assists in the initial assembly of the annular locking ring 60 to the securing collar 10.

Figure 4:
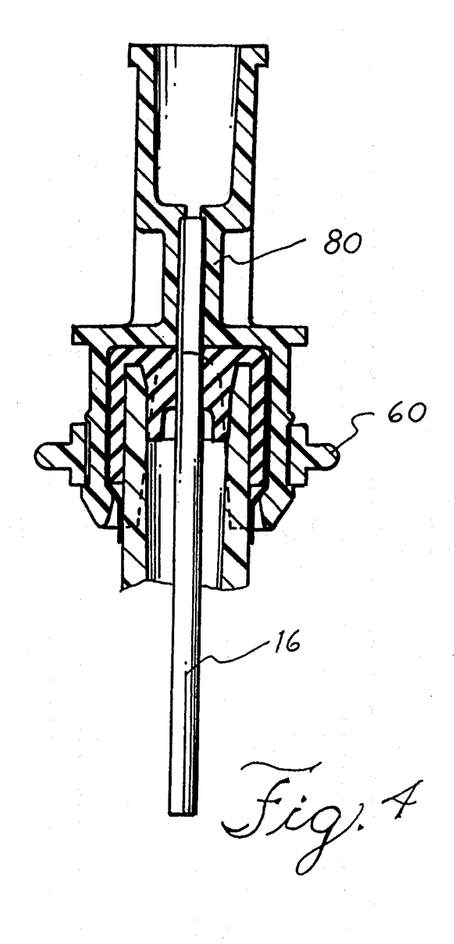
FIG. 4 is a cross-section of an alternative embodiment of the securing collar of the present invention that is integrally formed with a cannula connector.

FIG. 4 shows an embodiment having an integrally molded cannula hub and securing collar housing 80. The cannula 16 is insert molded or bonded in the integral cannula hub and securing collar housing 80 during manufacture. The device requires no further assembly other than to position the annular locking ring 60 on the splayed tubular collar 44.

Figure 5:
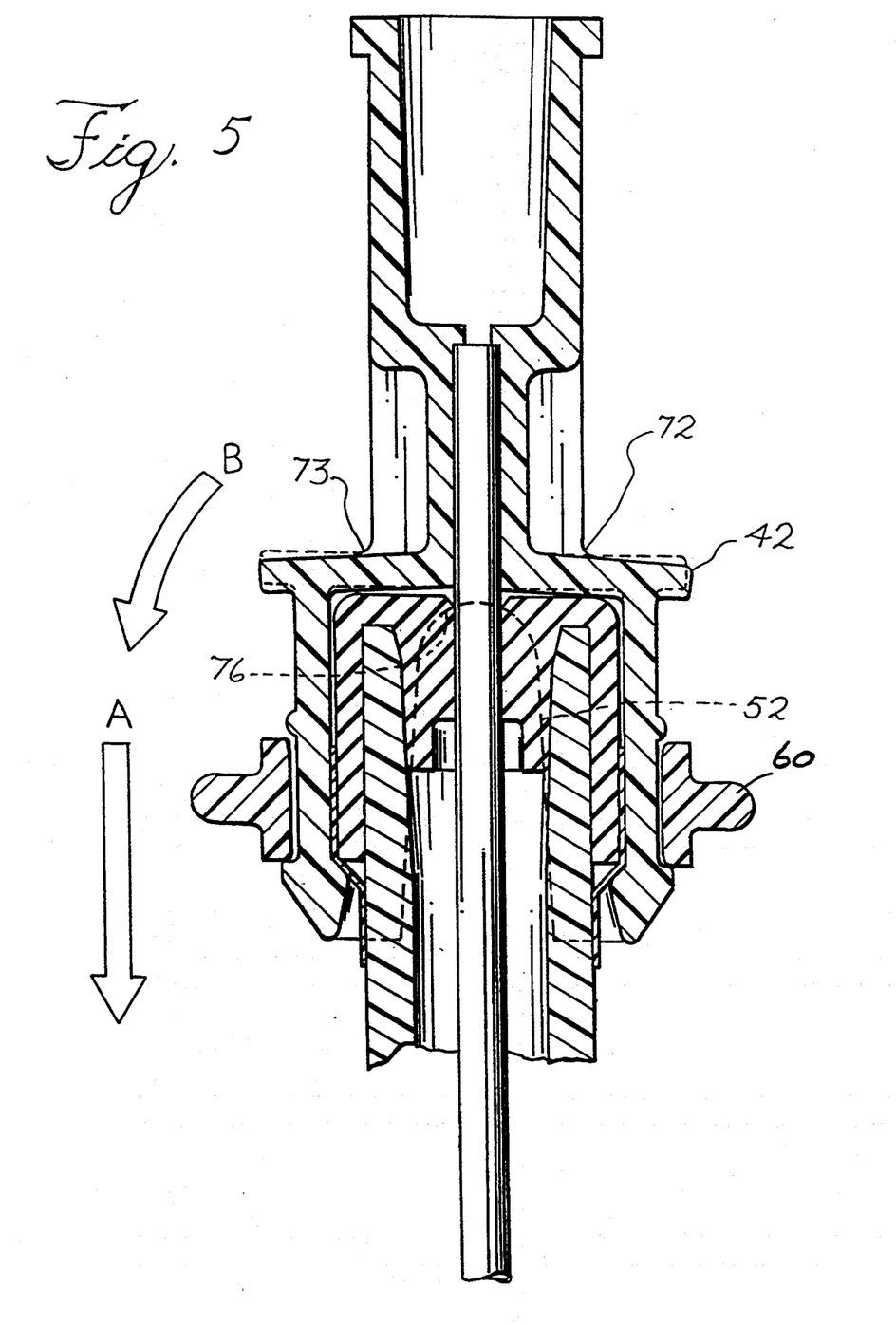
FIG. 5 is an enlarged view of FIG. 4 showing the deflection of the radially extending flange in the secured position.

FIG. 5 is an enlarged view of FIG. 4 and shows an advantage of the embodiment of the present invention having two diametrically opposite notches or recesses 52 forming two splayed collar segments 50. In this embodiment, the flexure lines of the splayed collar segments is along lines at or near 72 and 73 and parallel to the line between the rounded terminal ends 76 of the elongated recesses 52 (shown in phantom) in the tubular collar 44. Thus, in this embodiment, the two collar segments 50 of the tubular collar 44 are resiliently deflected along radially extending flange 42, as shown by arrow B, as the locking ring 60 is slid forward as shown by arrow A.

For other embodiments of the securing collar having other than two diametrically opposite recesses 52, such as those defining one or three or more segments 50, the flexure position is more likely to be on the tubular collar 44, resulting in a radially inward bending of the tubular segments 56 and 58 rather than a deflection of the radially extending flange 42.

As illustrated in FIG. 6, another composite embodiment of the invention is shown having a sharp cannula 23 that is wholly contained within a protective shroud 74 extending from the tubular collar 44 so as to prevent accidental needle stick. Thus the tubular collar 44 and the protective shroud portion 74 function together as a securing apparatus and a needle protecting apparatus.

Another alternative embodiment of the invention also seen in FIG. 6 includes an integral shoulder 55 at a larger diameter second (or distal) tubular portion 59 of the tubular collar 44. The larger diameter portion causes the annular locking ring to force or cam the second tubular portion 59 radially inward to engage the shoulder 32 of the second connector 14.

Figure 7:
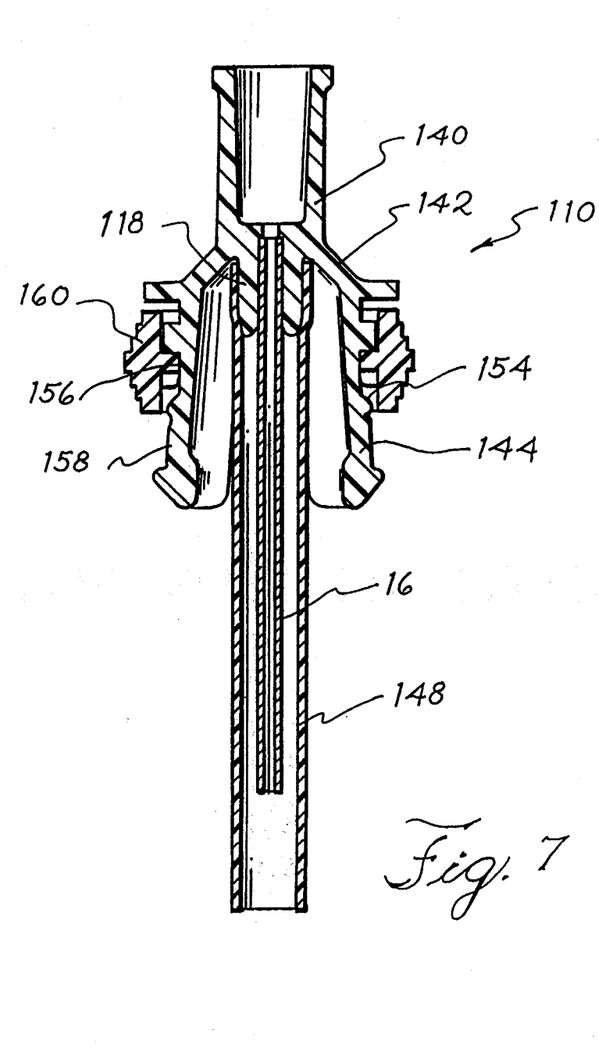
FIG. 7 is a cross section of the preferred embodiment of the present invention including a securing collar integrally manufactured or molded with a cannula connector.

FIG. 7 shows the preferred embodiment of the securing collar 110 of the present invention integrally molded with a cannula connector 12. In this preferred embodiment, the tubular housing 140 and a generally radial flange 142 of the securing collar 110 are injection molded integral with the cannula 16 to form the cannula hub 118. The outside diameter of the second tubular portion 158 is made larger than the outside diameter of the first tubular portion 156. A protective cannula sheath 148 is removably positioned over the cannula 16.

Figure 8:
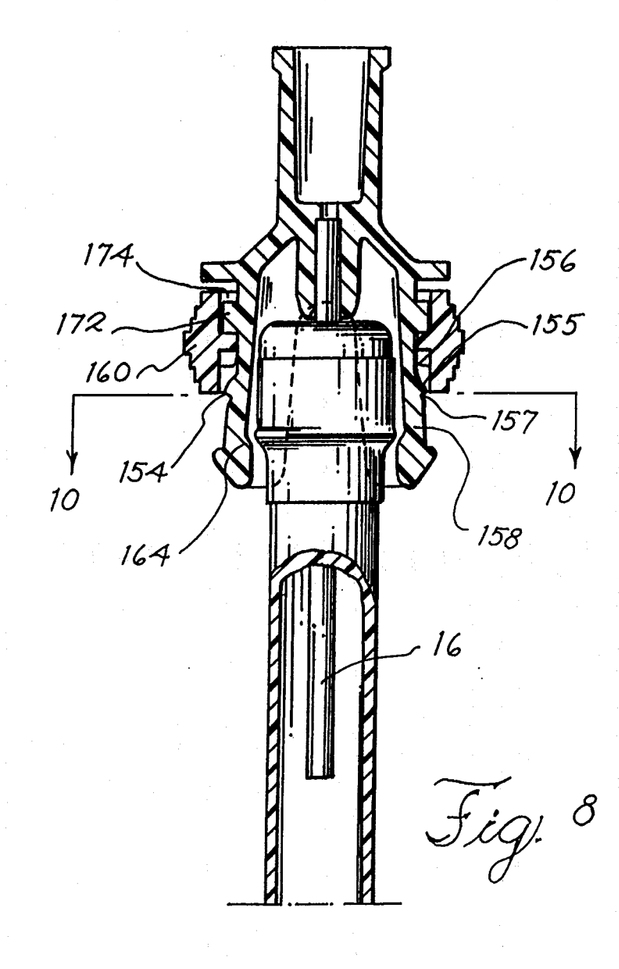
FIG. 8 is a cross section of the preferred embodiment of the integral securing collar and cannula connector of FIG. 7 with the connector engaged in fluid flow communication but with the securing collar unsecured to the reseal connector.
Figure 9:
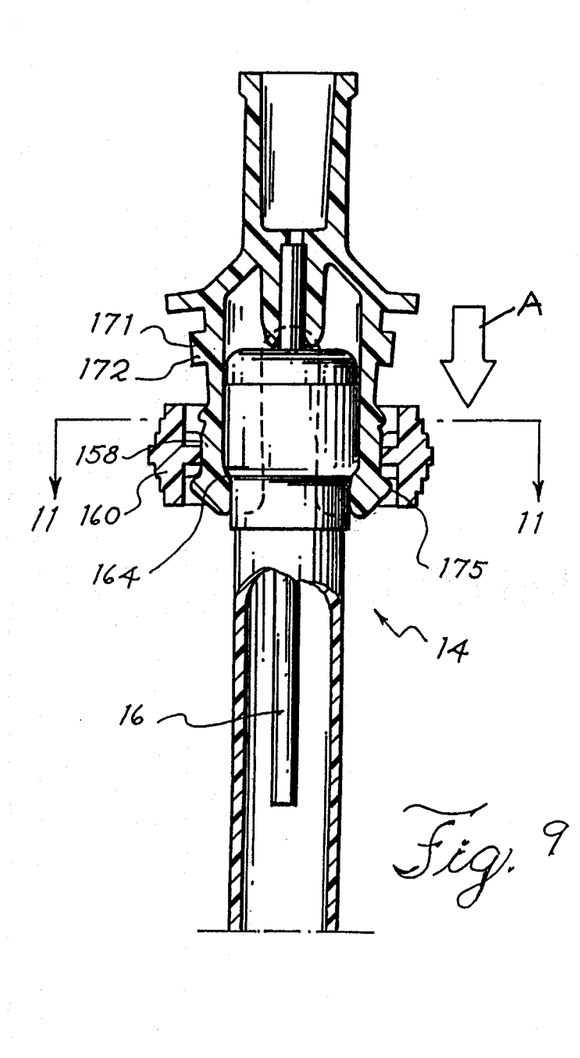
FIG. 9 is a cross section of the preferred embodiment of the integral securing collar and cannula connector of FIG. 7 with the connector engaged in fluid flow communication and with the securing collar secured to the reseal connector.

Referring now to FIGS. 8 and 9, when the annular locking ring 160 of the embodiment of FIG. 8 is slid from the first tubular portion 156 in FIG. 8 to the second tubular portion 158 in FIG. 9 by an axially applied force shown by arrow A, the annular locking ring 160 forces at least the second tubular portion 158 radially inward to contact the second connector 14 as seen in FIG. 9. The first tubular portion 156 may also move radially inward, depending on the construction and tolerances.

A transition portion 154 of the securing collar 110 is constructed between the first and second tubular portions to assist and then retain the annular locking ring 160 on the second tubular portion 158 as the annular locking ring is manually manipulated to the second tubular portion (which is also the secured position). The transition portion 154 includes an inclined ramp 155 on the proximal side of the transition portion to assist the annular locking ring 160 in moving over the transition portion 154 to the second splayed tubular portion 158.

Figure 10:
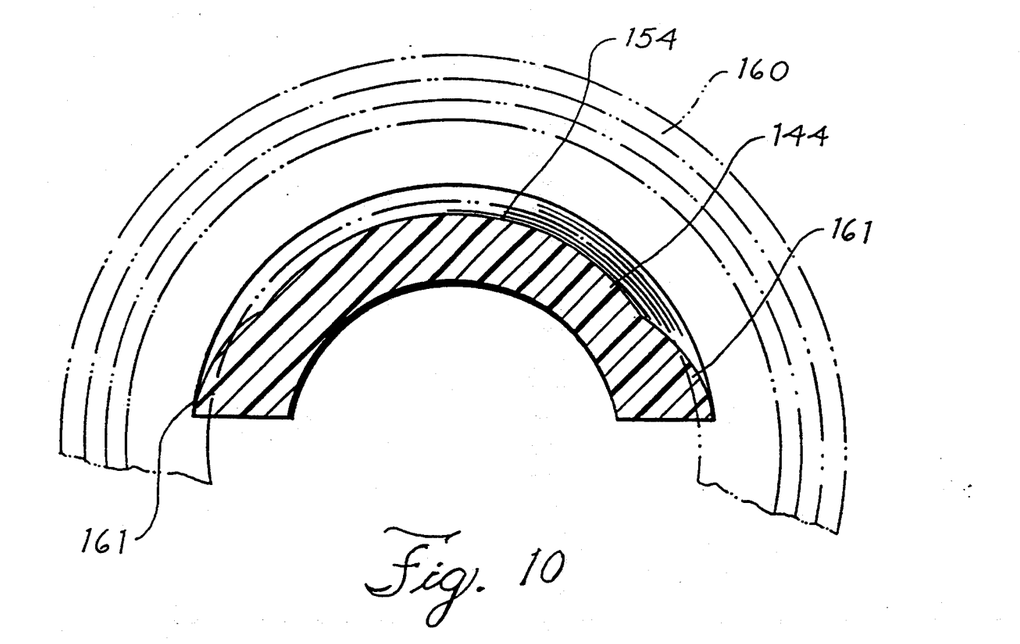
FIG. 10 is a schematic partial sectional view of the annular locking ring and the splayed collar of FIG. 8 in the unsecured position.
Figure 11:
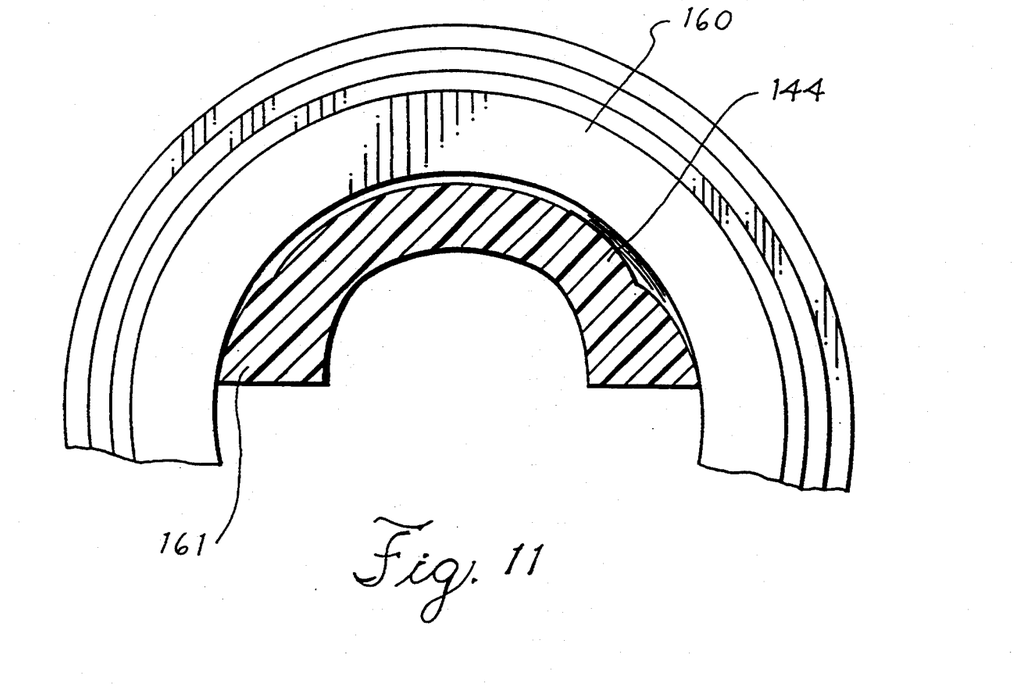
FIG. 11 is a schematic partial sectional view of the annular locking ring and the splayed collar of FIG. 9 in the secured position.

The transition portion 154 also includes a steep retaining shoulder 157 that has a larger outer dimension than the outer diameter of the second tubular portion 158. As best seen in FIGS. 10 and 11, the transition portion 154 preferably includes a set of four discrete bumps 161 (only two bumps being shown) circumferentially position at or near the midpoint of the tubular collar 144 and immediately adjacent the longitudinal notches 152.

The securing collar 110 also includes structure for limiting rotation of the annular locking ring 160 relative to the tubular housing 140 of the connector 12 when the annular locking ring 160 is positioned on the first tubular portion 156. For example, in FIG. 12, the cannula connector 12 is initially attached to the IV tubing set 170, by pushing on the connector 12 as shown by arrow F and by rotating the connector 12 as shown by arrow C. Furthermore, it is desirable that the annular locking ring 160 not be able to rotate relative to the tubular housing 140. Preferably the rotation limiting structure as shown in FIGS. 8 and 9 is a raised longitudinal tab 172 on an outer surface of the first tubular portion 156 and a mating slot 174 on an inner surface of the annular locking ring 160. To disconnect the connector 12 from the tubing set, as shown in FIG. 13, the connector 12 is rotated in an opposite direction as shown by arrow D, while an axial pull is provided as shown by arrow G.

Also as shown in FIGS. 8 and 9, the second tubular portion 158 of the tubular securing collar also has an undercut flange 164 on a distal end of the inner surface for engaging a second connector 14 when the second tubular portion 158 is forced radially inward by the annular locking ring 160 as best seen in FIG. 9.

In the preferred embodiment, the annular portion 171 associated with the raised tab 172 functions as an axial stop to retain the annular locking ring 160 on the first tubular portion 156. Likewise annular lip 175 on the outer distal surface of the second tubular portion 158 functions as another axial stop to particularly retain the annular locking ring 160 on the second tubular portion 158.

As discussed, the preferred embodiment of the securing apparatus of the present invention is an injection molded splayed collar and hub integrally manufactured with the cannula connector 12.

In other embodiments, the securing apparatus 10 is injection molded separately and can be added later to an individual cannula connector 12, either in the assembly plant or in the hospital, for example.

Figure 12:
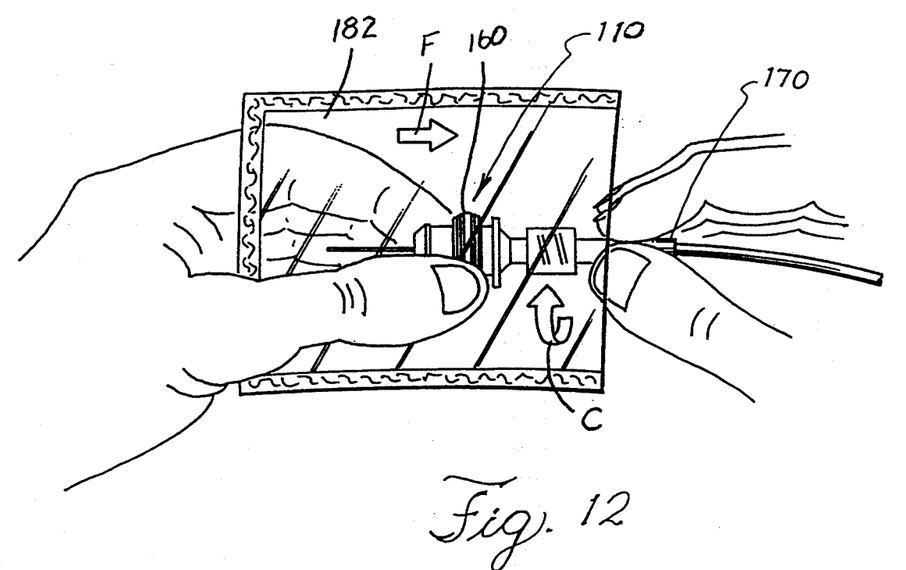
FIG. 12 is a schematic depiction of the cannula connector and securing collar of the present invention during an initial connection of the connector to an IV tubing set.
Figure 13:
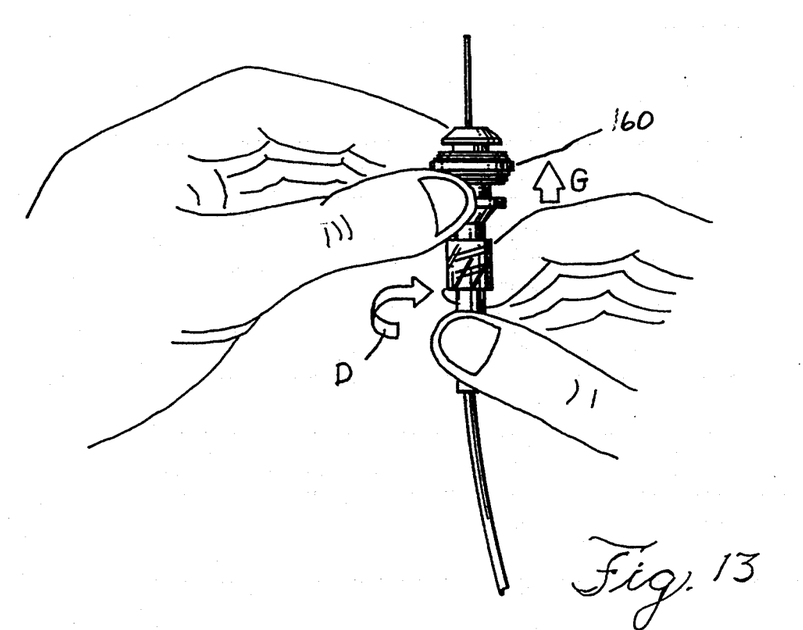
FIG. 13 is a schematic depiction of the cannula connector and securing collar of the present invention during disconnection of the connector from the IV tubing set.

The assembled cannula connector 12 and securing collar 10 is packaged and sterilized in a conventional flexible package 182, for example as shown in FIG. 12.

In use, as shown in FIGS. 1-3 and 7-9 the cannula connector 12 is inserted into the reseal connector 14 and the tubular collar 44/144 of the securing collar 10/110 is axially moved forward so that the splayed tubular collar 44/144 covers the annular shoulder portion 32 on the second connector 14. The annular locking ring 60/160 is then slid forward on the tubular collar 44/144 over the transition portion 54/154 to force the distal splayed collar segments 58/158 radially inward. The securing collar 10/110 thus secures the first connector 12 to the second connector 14.

With the use of the securing collar 10/110 according to the present invention, the axial force necessary to disengage the cannula connector 12 from the reseal connector 14 is increased from a minimal force to a force which is sufficient to resist most accidental disconnection situations.

The preferred material for the securing apparatus and connector is polypropylene or polyethylene. These materials are readily injection molded.

An advantage of the splayed end of the tubular collar is that the splay compensates for various reseal septums and various dimensional tolerances in like-type reseal septums.

In operation, the securing apparatus of the present invention can be readily engaged and disengaged from tubular reseal connectors of the rolled-over reseal type.

While several embodiments of the invention have been described, modifications within the scope of the present invention will be readily apparent to one of ordinary skill in the art. For example, the securing collar of the present invention may be used with any of the known fluid flow connectors such as sharp needles and unpierced reseals or blunt cannula and prepierced reseals although the preferred connector shown in the disclosed embodiments are primarily disclosed with respect to blunt cannula and prepierced reseals. All such modifications are intended to be covered by scope of the accompanying claims.

We claim:

1. A securable collar assembly for use with a fluid connector having an axially forward extending cannula for securably connecting the fluid connector to a tubular conduit having a septum at a terminal end and a radial shoulder proximate the septum, the collar assembly comprising:

a tubular housing axially engaged with the fluid connector so that the cannula of the fluid connector extends axially forward from the housing;

a generally radially extending, resiliently deflectable flange extending from the housing;

a hollow generally cylindrical collar extending longitudinally from the flange and coaxially with the cannula to an open forward end;

the hollow collar having an inner surface defining a bore for receiving the terminal end of the tubular conduit and a radially inward extending lip on the inner surface of the collar at the open forward end of the collar;

the collar having an outer surface including a first portion adjacent the flange having a first maximum diameter and a second portion between the first portion and the open end of the collar having a second minimum diameter which is larger than the first maximum diameter;

the collar having two diametrically opposed notches, each notch extending longitudinally rearward from the open forward end of the collar through the first and second portions of the collar to a notch closed end adjacent the flange so as to divide the collar into two longitudinal semi-cylindrical segments; and a ring longitudinally slidable along the outer surface of the collar from a first rear position on the first portion to a second forward position on the second portion, the ring having an inner diameter which is smaller than the second minimum diameter of the collar so as to compress the outer surface of the second portion when the ring is slid to the second forward position so as to pivot the two longitudinal segments of the collar radially inward at the deflectable flange so that the inward lip at the open forward end of the collar engages the radial shoulder of the tubular conduit.

2. The collar assembly of claim 1 wherein the longitudinal segments pivot along a portion of the radial flange, the flange portion being generally parallel to a longitudinal plane which bisects both longitudinal notches.

3. The collar assembly of claim 2 wherein at least the second portion of the outer surface of the collar is frustoconical-shaped.

4. The collar assembly of claim 3 further including means on the collar for restraining the slidable ring in the first and second positions.

5. The collar assembly of claim 4 wherein the restraining means includes at least one outward projection located between the first and second portions, and wherein at least one outward projection is inclined radially outward from both the first maximum diameter and second minimum diameter.

6. The collar assembly of claim 5 wherein the restraining means includes two outward projections, each projection on a separate one of the two longitudinal segments and each projection flanking a separate one of the two longitudinal notches.

7. The collar assembly of claim 4 further including means for limiting the relative rotation of the sliding ring on the collar in the first rear position.

8. The collar assembly of claim 7 wherein the rotation limiting means is a slot on the slidable ring constructed and arranged to axially register in a raised tab on the outer surface of first portion of the collar.

9. The collar assembly of claim 4 wherein at least a first portion of the inner surface of the collar adjacent the open end of the collar is frustoconical-shaped.

10. The collar assembly of claim 9 further including a radially outward extending shoulder on the outer surface of the second portion at the open forward end of the collar to prevent axial removal of the ring from the collar when the ring is in the second forward position.

11. The collar assembly of claim 3 wherein the first portion of the outer surface of the collar is frustoconical-shaped.

12. The collar assembly of claim 11 further including means on the collar for restraining the slidable ring in the first and second positions wherein the restraining means includes at least one outward projection located between the first and second positions, the projection inclined radially outward from both the first maximum diameter and the second minimum diameter.

13. The collar assembly of claim 12 wherein the first and second portions of the outer surface of the collar is a continuous frustoconical-shape.

14. The collar assembly of claim 13 wherein the inner surface of the collar is frustoconical-shaped.

15. The collar assembly of claim 14 further including a radially outward extending lip on the outer surface of the second portion at the open end of the collar to prevent axial removal of the ring from the collar when the ring is in the second forward position.

* * * * *